United States Patent
Rogers et al.

(10) Patent No.: US 10,086,212 B2
(45) Date of Patent: Oct. 2, 2018

(54) CONTINUOUS LOW IRRADIANCE PHOTODYNAMIC THERAPY LIGHT BANDAGE

(75) Inventors: Gary S. Rogers, Wenham, MA (US); Samuel L. Hill, Somerville, MA (US); Thomas A. Dowling, Sturbridge, MA (US)

(73) Assignee: ROGERS SCIENCES, INC., Beverly, MA (US)

( * ) Notice: Subject to any disclaimer, the term of this patent is extended or adjusted under 35 U.S.C. 154(b) by 0 days.

(21) Appl. No.: 13/479,926

(22) Filed: May 24, 2012

(65) Prior Publication Data

US 2012/0303101 A1 Nov. 29, 2012

Related U.S. Application Data

(60) Provisional application No. 61/490,159, filed on May 26, 2011.

(51) Int. Cl.
*A61N 5/06* (2006.01)
*A61B 18/22* (2006.01)

(52) U.S. Cl.
CPC ...... *A61N 5/062* (2013.01); *A61B 2018/2244* (2013.01); *A61B 2018/2261* (2013.01); *A61N 5/0616* (2013.01); *A61N 2005/063* (2013.01); *A61N 2005/0645* (2013.01); *A61N 2005/0647* (2013.01); *A61N 2005/0651* (2013.01); *A61N 2005/0653* (2013.01); *A61N 2005/0662* (2013.01)

(58) Field of Classification Search
CPC .. A61B 2018/00452; A61B 2018/2244; A61B 2018/2261; A61N 5/06; A61N 5/062; A61N 5/0616; A61N 5/0624; A61N 2005/005; A61N 2005/063; A61N 2005/0645; A61F 13/0202–13/0213; A61F 13/022
USPC ...... 606/9, 16, 17; 607/88–94; 362/554, 556
See application file for complete search history.

(56) References Cited

U.S. PATENT DOCUMENTS

| | | | | |
|---|---|---|---|---|
| 4,391,683 A | * | 7/1983 | Buckley et al. | 205/655 |
| 4,761,047 A | * | 8/1988 | Mori | 607/88 |
| 5,301,063 A | * | 4/1994 | Tohmon | 359/619 |
| 5,616,140 A | * | 4/1997 | Prescott | 606/10 |
| 6,231,593 B1 | | 5/2001 | Meserol | |

(Continued)

FOREIGN PATENT DOCUMENTS

| | | |
|---|---|---|
| GB | 2185188 A | 7/1987 |
| WO | 200213712 A2 | 2/2002 |

OTHER PUBLICATIONS

K. Imen, C. Lee, Y. Yang, S. Allen, and A. Ghosh, "Laser-fabricated fiber-optic taps," Opt. Lett. 15, 950-952 (1990).*

(Continued)

*Primary Examiner* — Nathan J Jenness
(74) *Attorney, Agent, or Firm* — Gesmer Updegrove LLP

(57) ABSTRACT

A system for photodynamic therapy is provided that includes a light delivery device that delivers the illumination necessary to perform photodynamic therapy. The light delivery device includes one or more etched fibers arranged to illuminate a selective region of a body for photodynamic therapy. An illumination device is coupled to the light delivery device to provide the necessary illumination to the light delivery device.

10 Claims, 9 Drawing Sheets

(56) References Cited

U.S. PATENT DOCUMENTS

| | | | |
|---|---|---|---|
| 7,174,077 B1* | 2/2007 | Howard | G02B 6/262 362/551 |
| 7,304,201 B2 | 4/2007 | Holloway et al. | |
| 7,686,839 B2 | 3/2010 | Parker | |
| 2002/0183811 A1* | 12/2002 | Irwin | 607/94 |
| 2003/0009205 A1* | 1/2003 | Biel | 607/88 |
| 2005/0165462 A1* | 7/2005 | Bays et al. | 607/88 |
| 2006/0173514 A1* | 8/2006 | Biel et al. | 607/88 |
| 2007/0233208 A1* | 10/2007 | Kurtz et al. | 607/88 |
| 2007/0263975 A1 | 11/2007 | Boutoussov et al. | |
| 2007/0288071 A1* | 12/2007 | Rogers | 607/88 |
| 2008/0015553 A1 | 1/2008 | Zacharias | |
| 2009/0161311 A1* | 6/2009 | Tseng | 361/679.47 |
| 2009/0175576 A1 | 7/2009 | Tang | |
| 2012/0065712 A1* | 3/2012 | Rivera et al. | 607/89 |

OTHER PUBLICATIONS

Written Opinion and International Search Report dated Jul. 24, 2012 in connection with PCT Application No. PCT/US12/039347.

International Preliminary Report on Patentability issued in connection with PCT Application No. PCT/US12/039347 dated Dec. 5, 2013.

Examiner's Report issued in co-pending Australian Patent Application No. 2012258675 dated Dec. 2, 2015.

Examiner's Report issued in co-pending Canadian Patent Application No. 2,837,332 dated Apr. 15, 2015.

Examiner's Report issued in co-pending European Patent Application No. 12724515.7 dated Mar. 16, 2015.

Examiner's Report dated Mar. 23, 2016 in Canadian Patent Application No. 2,837,332.

European Communication dated Mar. 23, 2016 in related European Patent Application No. 12724515.7.

Australian Patent Examination Report dated Oct. 2, 2015 in related Australian Patent Application No. 2012258675.

Notice of Grant issued by the Australian Patent Office dated Jul. 7, 2016 in connection with Australian Patent Application No. 2012258675, single page, no claims provided.

EP Communication issued in EP Patent Application No. 12 724 515.7 dated Sep. 30, 2016.

Examiner's Report issued in related Canadian Patent Application No. 2837332 dated Apr. 3, 2017.

* cited by examiner

| SPECIFICATION | MIN | MAX | METRIC |
|---|---|---|---|
| Illumination Wavelength | 400 | 850 | nm |
| LDD Pad Width | 0.75 | 1000 | mm |
| LDD Pad Height | 5 | 1000 | mm |
| Bend Radius — Width | 8 | 0.5 | mm |
| Bend Radius — Height | 8 | 50 | cm |
| Accuracy | | | $uW/cm^2$ at each measurement point within +/-20% of the mean. $uW/cm^2$ |
| Repeatability | | | $uW/cm^2$ at each measurement point within +/-10% of the median over 3 distinct measurements |
| Transmission Loss | - | 150 | dB/km |
| Tensile Strength | - | 50 | N |
| Coupling Configuration | | | Spherical Lens, Cylindrical Lens Coupling with Fiber Optic Input from Light Source |
| Coupling Efficiency | 20% | 7.5% | Output uW/Input uW |
| Temperature Range | -55 | 70 | C |
| Fiber-Plastic | | | Mitsubishi Rayon co., Ltd. Eska Polymer Optical Fiber |
| Sheath/Light Blocking | > 90% | | |

FIG. 2

CONTINUOUS LOW IRRADIANCE PHOTODYNAMIC THERAPY LIGHT BANDAGE

PRIORITY INFORMATION

This application claims priority from provisional application Ser. No. 61/490,159 filed May 26, 2011, which is incorporated herein by reference in its entirety.

BACKGROUND OF THE INVENTION

The invention is related to the field of photodynamic therapy (PDT), and in particular to a light delivery device (LDD) used in PDT.

In the medical device field there are numerous techniques to deliver light to perform a medical procedure, but the two most common techniques are direct and focused illumination. Direct illumination occurs with a bare or diffused light source placed a distance of several centimeters to meters from the patient. Direct Illumination devices are rarely attached to the patient. In general, the patient is required to position themselves to the illumination source. Examples of light delivery devices that fall within this category include conventional phototherapy units, such as the standard light box and hand/foot units that emit UV-A, UV-B or narrow-band UV-B light.

Phototherapy units are used primarily for the treatment of inflammatory skin diseases such as psoriasis. The units are also used in conjunction with orally or topically administered psoralens that photoactivate with UV-A light in the treatment of severe psoriasis and extensive vitilligo. This treatment is known as PUVA (psoralen UV-A) therapy. For systemic diseases such as cutaneous lymphoma, graft versus host disease and systemic sclerosis, extracorporeal photophoresis is performed where the patient ingests the psoralen and the blood is exposed to the UV-A light outside the body and then re-infused into the patient. The DUSA (blue visible light) and Galderma-Metvix (red visible light) systems are used for the treatment of actinic keratoses (pre-malignant skin growths) and superficial basal cell carcinomas. They work via topical aminolevulinic acid (DUSA) and methyl-aminolevulinic acid PDT.

Focused illumination, both internal and external to the patient treatment site requires illumination that has an optical system to direct light from the illumination device to specific areas onto the patient, typically in a controlled beam shape and beam intensity. In many cases the optical system is composed of one or more optical fibers that use total internal reflection to collect light at one end of the fiber, transmit the light, and exit with a specific numeric aperture at the other end. Typically this approach requires larger fibers or an array of large fibers to illuminate large areas (>5 mm). Illuminating more than a single fiber requires sophisticated coupling of the light into the fibers. This coupling is usually inefficient and can have very low coupling efficiency (<10% efficiency). Similar to direct illumination, the focused illumination approaches are rarely done where a patient wears a device.

For FDA approved PDT indications, there are numerous light illumination devices meeting the direct and focused illumination schemes. For example, for Barrett's esophageal cancer treated with PDT, a focused illumination system is implemented using a fiber optic cable attached to a FDA approved laser system such as the Angio Dynamics PDT 630 nm laser. Alternatively, a direct illumination approach to PDT for actinic keratosis is done using similar devices such as DUSA's Blue-Light Phototherapy Lamp or Galderma's Aktilite which is also used for basal cell carcinoma skin cancer.

There are few wearable medical based illumination devices except for the Ambicare Health Ambulight PDT device that only covers a small area and has no degree of flexibility or conformity to anatomical features. The device is a pad of LEDs that are placed directly on the treatment area. This method of delivery does allow the system to be portable, but it places the illumination source directly on the patient causing thermal side effects.

Another device that is wearable, but displaces the illumination source and any generated heat from the source at a distance from the treatment site is a weaved collection of fiber optic cables that are bent sharply at several locations along the length of the fiber. The bending of the fiber cause light to leak from the fiber illuminating a small portion of a light illumination surface that consists of hundreds to thousands of these bent fibers. This weaved fiber approach provides imprecise quantities of light at the treatment site because the bending (the mechanism of light leakage) of the fiber is not uniform from bend to bend and the location of bending along similarly aligned fibers can be random from fiber to fiber.

SUMMARY OF THE INVENTION

According to one aspect of the invention, there is provided a system for photodynamic therapy. The system includes a light delivery device that delivers the illumination necessary to perform photodynamic therapy. The light delivery device includes one or more etched fibers arranged to illuminate a selective region of a body for photodynamic therapy. An illumination device is coupled to the light delivery device to provide the necessary illumination to the light delivery device.

According to another aspect of the invention, there is provided a method for performing photodynamic therapy. The method includes delivering illumination necessary to perform the photodynamic therapy using an illumination device. Also, the method includes coupling the illumination to a light delivery device having one or more etched fibers arranged to illuminate a selective region of a body, either internally or externally for photodynamic therapy.

BRIEF DESCRIPTION OF THE DRAWINGS

FIG. 2 is a table illustrating the specifications of the inventive LDD;

DETAILED DESCRIPTION OF THE INVENTION

The invention describes a novel light delivery device (LDD) that overcomes the technical hurdles to traditional fiber optic light application technologies, while in the process creating a lighter, thinner, flexible, scalable, and low cost device. The inventive LDD is created with precision patterning of one or more fibers such that light can leak from the fibers in a precise manner along the length of the fiber used in PDT treatments, such as continuous low irradiance photodynamic therapy (CLIPT) or the like. When the pattern is applied to a 10 cm wide array of 10 cm long fibers (creating the 10 cm² LDD pad where light emission occurs) it allows one to control light existence from a LDD pad to within +/−20% of the average irradiance compared to +28%/−37% for conventional systems. This benchmark guarantees even illumination and uniform results during treatment.

In the discussion hereinafter, CLIPT is described but it is noted other PDT-based therapies can be used.

Also, with the invention one is able to solve a key hurdle in using a laser illumination system where the beam is of greater intensity at the center and falls off (with a Gaussian profile) in intensity towards the edge of the beam. Traditionally, this would lead to an extreme high intensity hot spot in the center of the LDD pad and little illumination along the edges. By generating a pattern that has a reverse Gaussian profile one can allow the Gaussian beam to be suppressed in the center of the LDD and to match more closely with the uniformity along the edges of the LDD pad. This feature of illumination control is important as one is able to precisely control the amount of irradiance delivered to different anatomical regions on larger based LDDs or LDDs on complex anatomical sites (CAS) such as the ears, noses, eyelids, lips, fingers, toes, pre-tibial, and genitals In the process of developing the inventive light diffusion technology the mechanics of the LDD drastically changed allowing for bend radiuses less than 12 cm, a reference that approximates the radius of the chest wall for a 50th percentile female. Bending tests showed no long term effects on light uniformity after multiple 24 hr performance periods. Current testing has shown that LDDs using the inventive light diffusion technology with bending radiuses as low as 0.5 cm which would allow for various CLIPT treatments on complex anatomical sites such as the ears, eye lids, nose, fingers, toes, and genitals, as these locations will invoke curvatures, movement and other anatomical and functional challenges much different than the chest wall.

Figure 1:
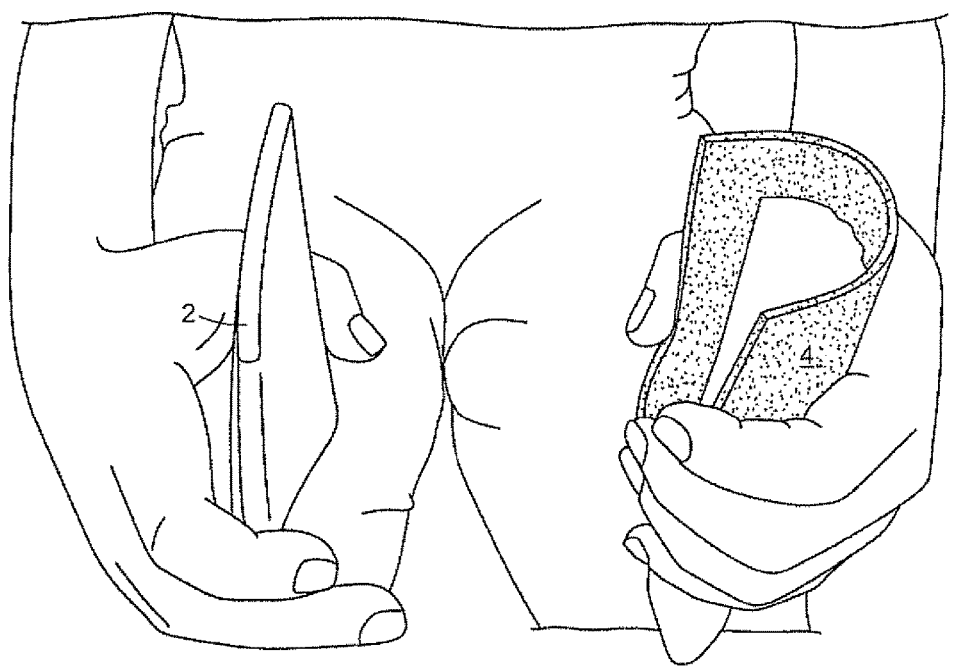
FIG. 1 is a photograph illustrating a comparison between a first generation LDD and the invention.

Thus, the invention allows for bending radiuses over several orders of magnitude allowing for light delivery for CLIPT treatments on external anatomical surfaces with tight bending radiuses such as ears, eye lids, noses, fingers, and toes, as well as internal anatomical features such as the esophagus or cervix. Additionally the LDD could be implantable and shaped to the liver or pancreas. An example of the comparison in flexibility of a first generation LDD 2 commonly used in the prior art to that of the novel LDD 4 is shown in FIG. 1. Moreover, a list of the novel LDD 4 operational specifications is given in Table 3 shown in FIG. 2.

Figure 3:
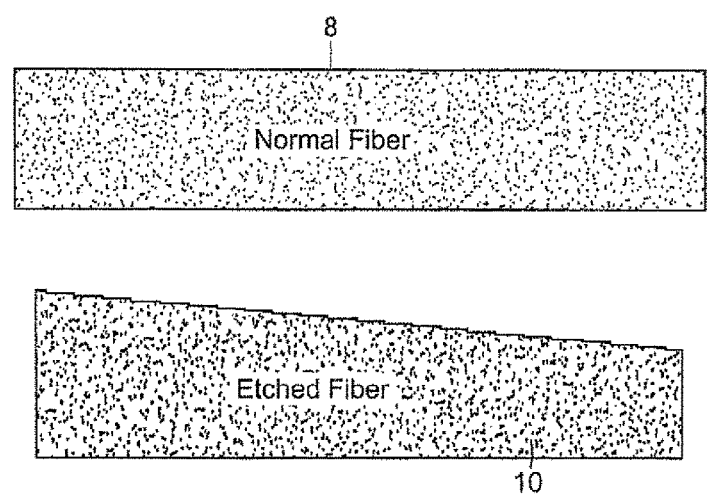
FIG. 3 is schematic diagram illustrating the laser cutter etching of a fiber used in accordance with the invention.

The first generation LDD was developed and fabricated using a bent fiber approach to cause imprecise light leakage at multiple bending points. To improve efficiency, reliability, and accuracy, an etched fiber 10 is formed by exposing a normal fiber 8 to an innovative process of light leakage, as shown in FIG. 3. The cladding or partially the core of the fiber 8 can be etched to form the etched fiber 10. The cut can be in one plane, multiple planes, or rotationally around the fiber 8. FIG. 3 shows etching in a single plane.

Traditionally, in a fiber optic cable light travels down the fiber until the end of the fiber at which point it exits with some convergence or divergence pattern. With precision etching of the fiber, it allows for predictable illumination along the length of one fiber in a linear or non-linear controlled output. Due to the etching process, similarly aligned fibers will have similar etching and performance such that an array of fibers can be stacked in a one-dimension, two-dimensional, or three-dimensional pattern for predictable and uniform illumination. Precision etching of the fiber also allows for non-continuous etching as well as continuous etching (as described) which allows for varying shape patterns and geometries to be etched into one or more fibers creating complex beam shaping illumination along the length of one or more fibers.

Traditionally, fibers could be etched by hand or non-motorized processes but the invention uses the precision and speed of a motorized laser cutter with the ability to cut in three-dimensions. The illumination output along the etching path can vary depending upon the depth of the cut (set by the power of the laser, focus of the laser, and the speed of the laser cut), the cut type (raster or vector), and the cut patterns (criss-cross, weave, etc) set in the laser cutter operation menu.

Figure 4:
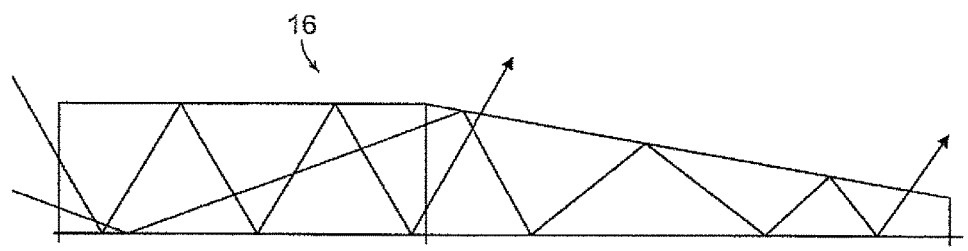
FIG. 4 is a schematic diagram illustrating light rays prorogating in the etched fiber formed in accordance with the invention.

A ray 15 of light injected into a fiber optic cable 16 can bounce along off each core/cladding or core/air interface without otherwise changing its direction due to total internal reflection, as shown in FIG. 4. If, however, one core/cladding or core/air interface is angled with respect to the other (as in the etch) so that the fiber optic cable 16 is shaped like a wedge, then each time the ray 15 bounces off the angled core/cladding or core/air interface its direction will change with respect to the planar interface. Repeated bounces can lead to the angle between the ray 15 and the interface normal getting progressively smaller until the critical angle at which rays undergo total internal reflection is reached, and the ray 15 can then pass through the interface and emerge from the fiber optic cable 16. Varying light output patterns can be achieved by the linearity or non-linearity of the etch including periodic versus continuous etches.

Figure 5:
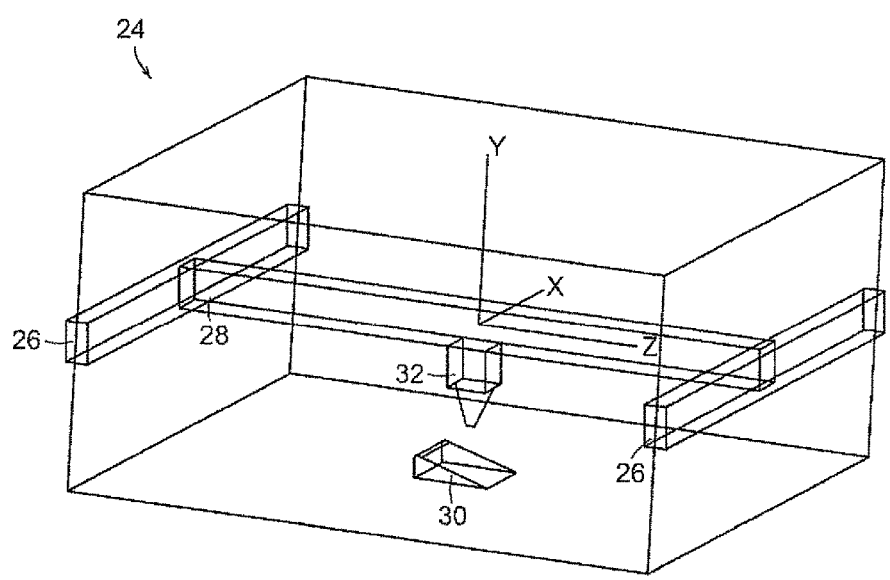
FIG. 5 is a schematic diagram illustrating the laser cutter arrangement used in accordance with the invention.

FIG. 5 shows an arrangement of a laser cutter 24 used to etch a fiber 30 in accordance with the invention. The laser cutter 24 includes a laser 32 on a 2D servo 26, 28 that allows for cuts to be made into the fiber 30 by adjusting the laser's focal length, power, etching or cutting speed, the type of cut (raster or vector) or varying the cut pattern. The laser cutter 24 is not novel, but the technique and patterns and the effect on the fiber 30 is novel. The ability to place the fiber 30 in a rotational chuck within the laser cutter 24 allows for cuts in three-dimensions, particularly rotational cuts allowing for complex cuts and illumination patterns. Rails 26, 28 allow the laser 32 to move front and back as well side to side.

This illumination effect from the etching process can occur on one fiber to make a single fiber LDD that can be used for small surface areas on the body such as around noses, ears, or fingers. If multiple fibers are placed next to each other in the laser cutter, they can be uniformly cut and then with an adhesive can make a larger surface that can cover large surface areas of the body.

Additionally, by stacking the fibers next to each other and then cutting a pattern into the fibers, these fibers can then be separated individually to make complex shapes providing even illumination. For example, the fibers can be arranged to make a stent that can be placed endoscopically in the body for treating esophageal cancer. Alternatively, the fibers can be arranged in a pattern around a mesh that could be implanted in the body around major organs/cavities to provide CLIPT/PDT illumination. For internal use of the LDD requires connecting the illumination source to the LDD externally, ideally through a sterile catheter.

The etch process can be performed on both glass and plastic fibers, however, plastic is preferred because of its ability to bend over tight bending radiuses without breaking or compromising irradiance over long CLIPT treatment sessions. Plus, the plastic fiber is biocompatible and does not require strenuous sterilization for patient reuse.

To provide additional light directionality from the fiber, a diffuser, ideally an off the shelf diffuser, can be placed over one or more fibers. The diffuser can help change the light behavior of one or more fibers particularly in conjunction with the etching process. For even illumination along the length of the fiber, the etch of the fiber can be made in such a way that the illumination exiting from the entire length of the fiber is constant.

This fiber optic etching approach to precision and uniform light delivery for CLIPT allows less fiber to be consumed compared to approaches in the prior art and it also makes the device thinner because the etch can be used on the thinnest fibers in the market. Also, with only a single 1-D array of fibers the LDD becomes flexible allowing it to curve naturally to the body. This makes it possible to curve the LDD to the chest wall, the neck, to a forearm or wrist, or to a leg or other very small anatomical areas with radius of curvatures as small as 0.25 mm.

Another approach to etching the fibers with the laser cutter is to use mechanical means to adjust the etching process rather than using the laser cutter settings. A mechanical fixture with an inclined ramp can be used to hold the fibers of the LDD in the laser cutter at various focal lengths of the laser. Various focal lengths can provide variation in the power which affects the depth of the laser cut along the fiber, thus creating an etched ramp along the length of the fiber. Depending on the ramp angle, the cut depth and light diffusion of one or more fiber optic cables can be changed. The mechanical ramp fixture is made of aluminum and is capable of holding or more fibers, however, in this fixture, only a one dimensional cut is allowed.

Figure 6A:
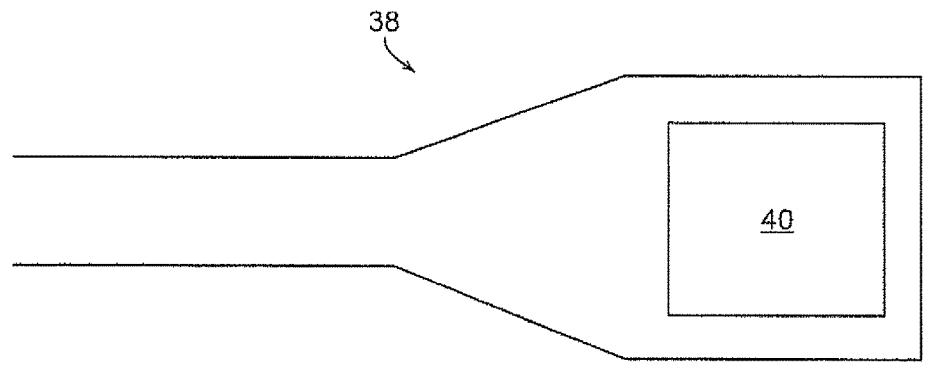
FIGS. 6A-6B are schematic diagrams illustrating the sheath top used in accordance with the invention.
Figure 6B:
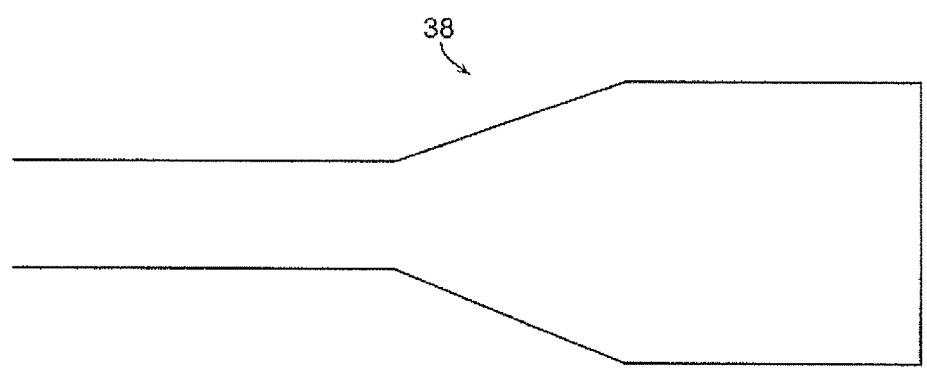

Once fabrication is completed the LDD pad fibers require adhesion to maintain rigidity, optical clarity, flexibility, and alignment. The adhesive material is off-the shelf. After adhesion, the LDD pad 40 is fitted to a biocompatible and non-flammable sheath top 38 as shown in FIG. 6A-6B. Note FIG. 6A is the top view of the sheath top 38 and FIG. 6B is the bottom view of the sheath top 38.

Figure 7:
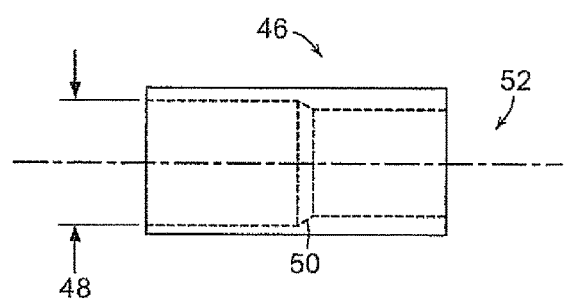
FIG. 7 is a schematic diagram illustrating an optical coupler used in accordance with the invention.

FIG. 7 shows an optical coupler 46 used in accordance with the invention. Once a LDD pad is assembled and into a fixed pattern, the proximal end 48 of the optical cables used in forming the LDD needs to be coupled to an illumination source (currently a laser) by the optical coupler 46. The optical coupler 46 can direct the light into the LDD by focusing the illumination in a line array 52 using a cylindrical lens optical system 50 or a LDD can collimate a circular beam into a circularly composed array of fibers. The fibers can be held in a circular array mount at the proximal end by means of a mechanical ring. Placement of the fibers is not critical if the beam uniformity from the coupler is uniform.

Figure 8:
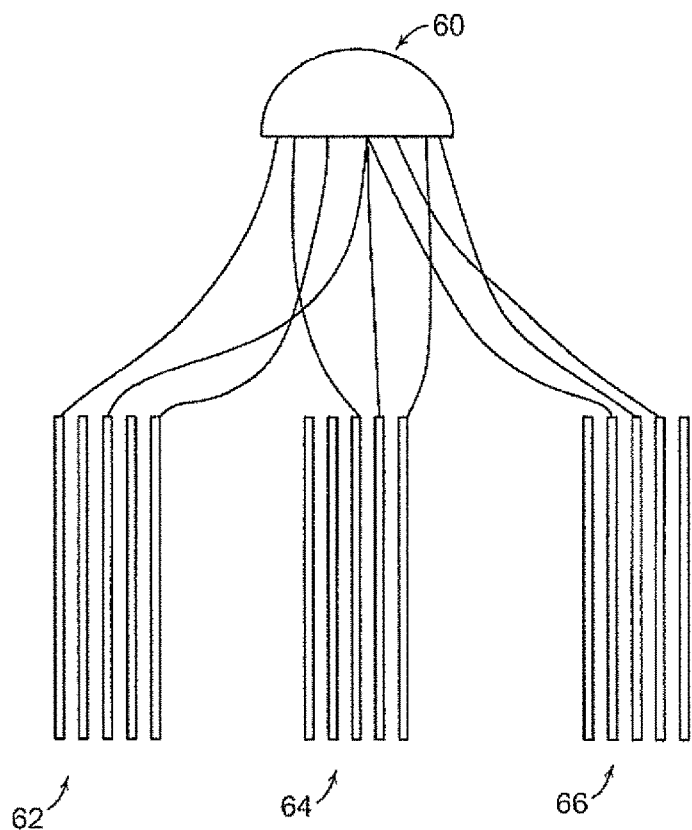
FIG. 8 is a schematic diagram illustrating a non-uniform placement of LDD to form a Gaussian beam.

FIG. 8 shows a non-uniform placement of a LDD to form a Gaussian beam. If the beam uniformity is not uniform or Gaussian, then fibers 62, 64, 66 from different regions of a LDD pad can be placed in different regions of the LDD mechanical holding ring 60. By placing the fibers 62, 64, 66 in precise locations along a non uniform beam, allows the user to dissipated hot spots by increasing or decreasing the irradiance at the pad. The coupling of the inventive LDD is similar to those in the prior art except the housing has been machined out of a light weight material rather than aluminum.

Figure 9:
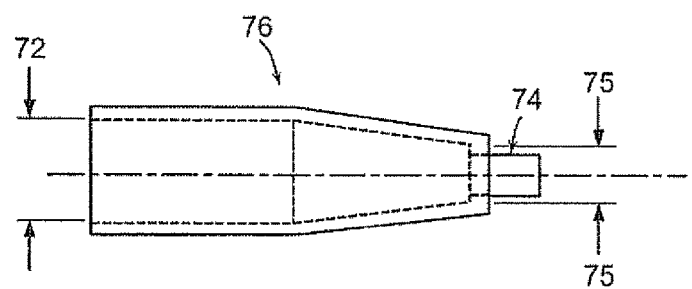
FIG. 9 is a schematic diagram illustrating SubMiniature version A (SMA) coupler used in accordance with the invention.

FIG. 9 shows another approach for coupling illumination into a LDD where no bulky glass or plastic optics are used. Since a LDD circular bundle 72 of optical fibers can be 0.5 cm in diameter, it can be fed to match the diameter of the SubMiniature version A (SMA) fiber Numerical Aperture output 74 using an optical coupler 76. However, this approach can have coupling efficiency loss as the SMA output 74 is diverging and can have different coupling effects for optical fibers on axis versus those optical fibers on the perimeter of a coupling ring 75.

A coupling housing unit can be made of Rydell or PEK, a very light weight and biocompatible plastic material. This reduces the weight drag attached to the LDD, which is important when a human subject is wearing the LDD in critical sites. Lowering the weight also makes the LDD more comfortable to wear over the extended CLIPT treatment which typically runs for 4 hours or more for one or more treatment days. For example, for chest wall progression of breast cancer, patients receive a single treatment of CLIPT for 24 hours with an irradiance ranging from 290 $\mu$W/cm$^2$ to 580 $\mu$W/cm$^2$.

Following in conjunction with the light diffusion technology and fabrication process above, an alternative embodiment is to etch fibers that are embedded into bandages with or without adhesive.

Figure 10A:
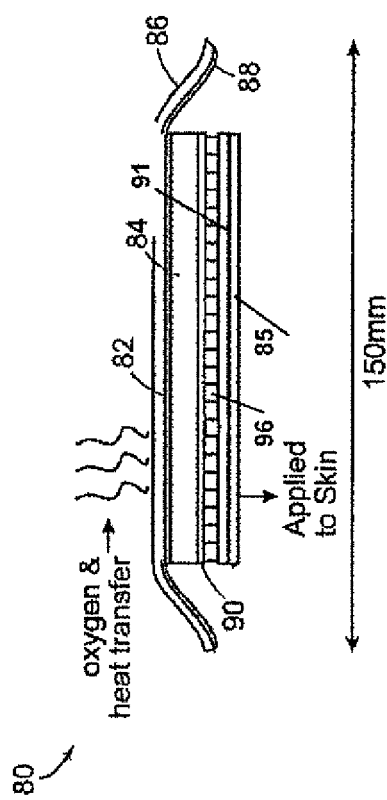
FIGS. 10A-10C are schematic diagrams illustrating a light bandage formed in accordance with the invention.
Figure 10C:
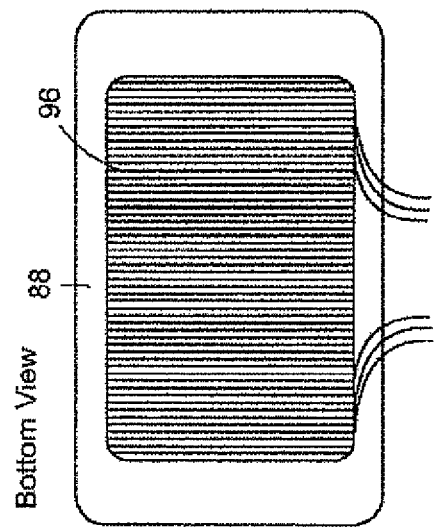
Figure 10B:
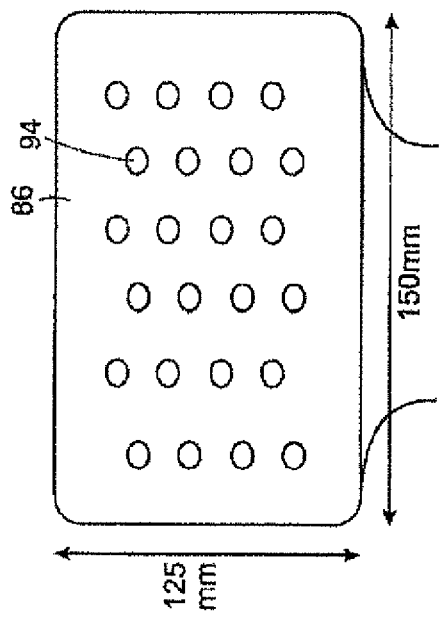

FIGS. 10A-10C show an example of a light bandage 80 formed in accordance with the invention. FIG. 10A is a side view of the light bandage 80 that includes a flexible polyurethane layer 86. The flexible polyurethane layer 86 permits oxygen and heat transfer to occur using a number of holes to be described hereinafter. A skin adhesive layer 88 is positioned beneath the flexible polyurethane layer 86 that connects to an opaque layer 82, having black flexible polyester, for blocking light. A first fluid absorbing layer 84 is positioned between the opaque layer 82 and a first adhesive layer 90. Fiber optic cables 96 are positioned between the first adhesive layer 90 and a second adhesive layer 91. A second fluid absorbing layer 85 is positioned underneath the second adhesive layer 91 that comes in direct contact or is applied to the skin. The first fluid absorbing layer 84 and the second fluid absorbing layer 85 can use fluid absorbing materials such as cotton or the like. The length of the light bandage can be 150 mm or smaller depending on the need.

FIG. 10B is the top view of the light bandage 80 which shows the holes 94 used in oxygen and heat transfer mentioned hereinbefore as well as the flexible polyurethane layer 86. FIG. 10C is the bottom view of the light bandage 80 which shows an exposed region of the light bandage 80 where the fiber optic cables 96 are positioned inside the exposed region that is surrounded by the skin adhesive layer 88.

The fiber optic cables 96 can be pre-etched and then adhered to either the adhesive or non-adhesive side of the light bandage 80 or applied directly to a non-adhesive bandage. The fiber optic cables 96 could also be embedded into the light bandage 80. Alternatively, the fiber optic cables 96 could be placed on any surface of the light bandage 80 or embedded in the light bandage 80 as well as the light bandage 80 and fiber optic cables 96 could be cut by the laser etching process. The laser etch cut may allow for mechanical features of the light bandage 80 while also creating the light diffusion pattern on the fiber optic cables 96.

The fiber optic cables 96 can be placed on any surface of the light bandage 80 or embedded but can be flexed in various geometric bending positions or be wrapped in circular loops to provide more flexibility to the light bandage 80. These complex shapes can help provide various mechanical and human factor conditions that may not be met with a straight fiber.

The light bandages with pre-etched or post-etched fiber optic cables can be of many different aerial sizes but would ideally be 1 cm$^2$, 5 cm$^2$, 10 cm$^2$, and 20 cm$^2$ in size. The light bandages with etched fiber optic cables could receive light from a fiber optic cable from an LED or laser light source. The fiber optic cables in the light bandage 80 can have a common input at one end of the bandage allowing for the coupling of the light through additional fiber optics or various other optical systems. The preferred method would be to couple light from LED light source via a SMA fiber attached to the LED output and connected to the light bandage.

The light bandage 80 could be used in similar applications and medical indications used throughout this application.

As part of the LDD or light bandage 80, the device could also act as a transdermal patch, a medicated adhesive patch that is placed on the skin to deliver a specific dose of medication through the skin and into the bloodstream. The medication in this application would be a photosensitive drug formulated to work in such a patch. The formulated drug would ideally have an aminolevulinic acid (ALA), methyl aminolevulinaate (MAL) or levulinic acid (LA) compound associated within the formula makeup of the photosensitizer. The LDD or light bandage could adhere via typical transdermal patch adhesives that have minimal effect on the photosensitizer.

An advantage of a transdermal drug delivery route over other types of medication delivery such as oral, topical, intravenous, intramuscular, etc. is that the patch provides a controlled release of the medication into the patient, usually through either a porous membrane covering a reservoir of medication or through body heat melting thin layers of medication embedded in the adhesive. Additionally, the patch allows for precise delivery of the drug to the treatment area. For CLIPT, this would entail precise delivery of the photosensitive drug to the treatment area.

An additional alternative embodiment of the LDD and the etching process on individual fibers is to mold or weave the fibers of the LDD into the shape of a stent, such as a circular mesh that would mold to the circular profile of the esophagus. In the case of treating internal applications such as PDT for Barrett's esophagitis and esophageal cancer, the light emitted from the LDD stent would be emitted outwardly. The fiber optic cable that would deliver light to the LDD stent is transmitted from the external light source to the stent along the patient's feeding tube. The feeding tube can be trans-nasal or trans-gastric.

As part of the CLIPT system and the need to make the wearable LDD portable, the illumination device generating the light going into the LDD must be portable. To do this, the invention can include a portable illumination device (PID).

Figure 11:
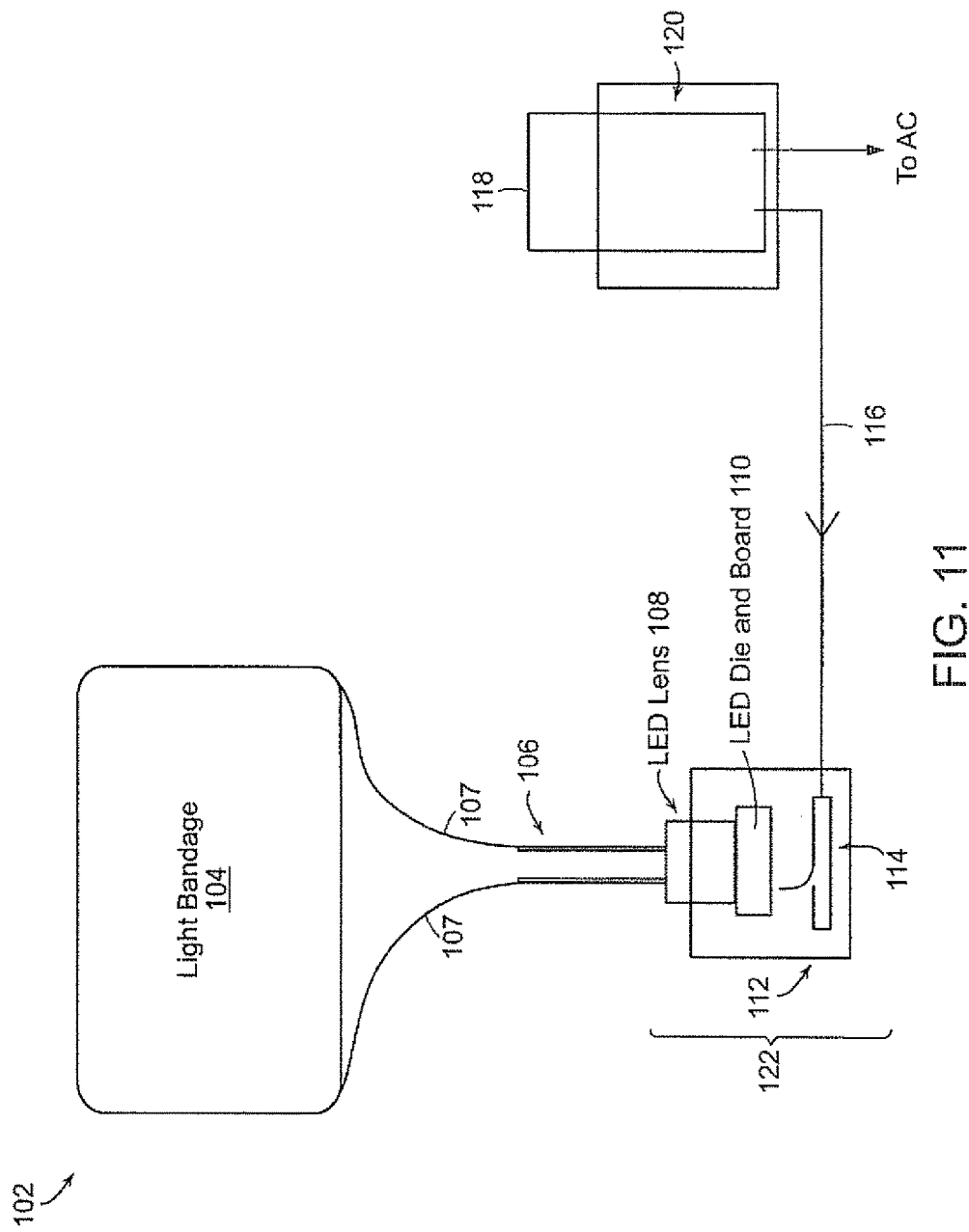
FIG. 11 is a schematic diagram illustrating a portable illumination device (PID) formed in accordance with the invention.

FIG. 11 shows a PID 102 formed in accordance with the invention. The PID 102 includes a Li-ion rechargeable battery 118 that is positioned in a battery holder and AC charger 120. Also, the battery holder 120 is coupled to an AC outlet for charging and includes a power cable that is coupled to an illumination unit 122. The illumination unit 122 includes a thermally isolating plastic housing that houses a power board 114 that is connected to the power cable 116. The power board 114 provides the appropriate power to a LED die and board 110 that runs a LED lens structure 108. The LED lens structure 108 provides illumination to a coupler unit 106 which is coupled to the fiber optic cables 107 of a light bandage 104. The light bandage 104 is similar to the light bandage 80 described hereinbefore.

Although one could use any light source that can match the wavelength activation spectrum of the PDT or CLIPT photosensitizing drug, an inexpensive, compact, and cooled light emitting diodes (LEDs) is used as opposed to a laser or laser diode. Although other various forms of LEDs can be used, such as organic LEDs (OLEDs), a standard, high lumen/watt efficient LEDs is used. The illumination unit 122 can include a red 630 nm 4-to-16-die 0-5 W LED PID. The wavelength output can be modified to work at other wavelengths by using the appropriate LED. The PID is compact and can be strapped to a human subject by means of a belt clip or in a fanny pack The PID uses two methods to reduce heat over traditional LED illumination devices. One method uses a coolant gel at the board level allowing for reduced heat buildup at circuit connections. The second method uses a light and compact heat sink fan on the back side of the illumination unit 122.

In conjunction with the etched fiber approach, an advantage of our wearable illumination system design is that the fiber optic cables transport the illumination from the illumination source at some distance to the tissue of a treatment site. This is different than typical approaches where the illumination source, in this case an LED illuminator, is placed directly in contact or in close proximity with the tissue treatment site Direct contact illumination in high-energy PDT and also in CLIPT generates a significant amount of heat because the illumination source is typically inefficient at converting a great amount of electrical power into optical power. When the conversion is extremely inefficient, the electrical power not converted to optical power is dissipated as heat. Extreme heat can cause cell damage to healthy tissue. An example of this effect has been recently seen in high-energy photodynamic therapy clinical studies by Light Sciences Oncology in which they have tried to place high intensity LED illumination sources at the treatment site of patients with Glioma which has led to severe heat based side effects on healthy cells and overall success of their therapy products.

Although the CLIPT treatment can use a low-energy fluence approach and the low-thermal high efficiency LED modules can reduce the side effects of heat dramatically by moving the LED illumination off the tissue treatment site and using the etched fiber method to deliver the light to the treatment site from a distance. External tissue temperature increases have been maintained to within 1-deg C. where several guidelines indicate that a delta change in temperature of less than 3-deg C. will not cause tissue damage on most patients.

Figure 12B:
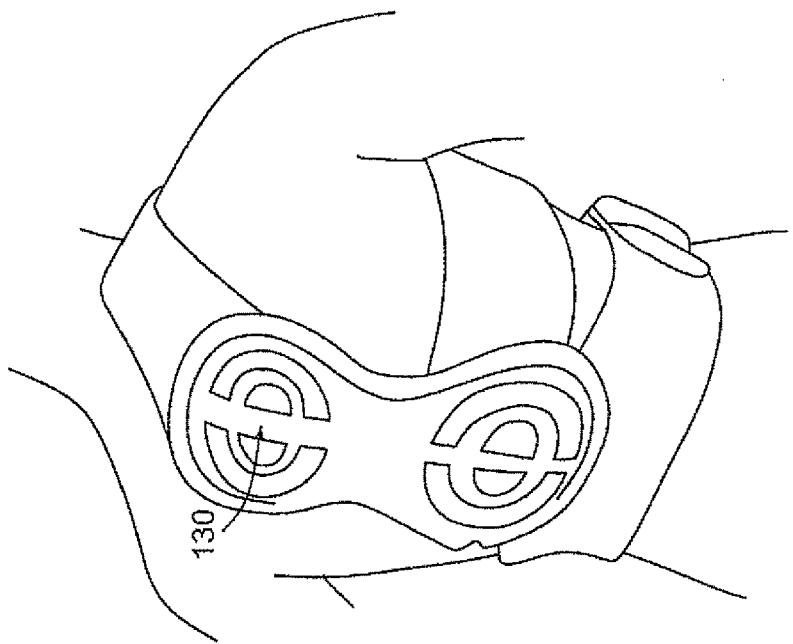
FIGS. 12A-12B are schematic diagrams illustrating a chest harness having a LDD formed in accordance with the invention.
Figure 12A:
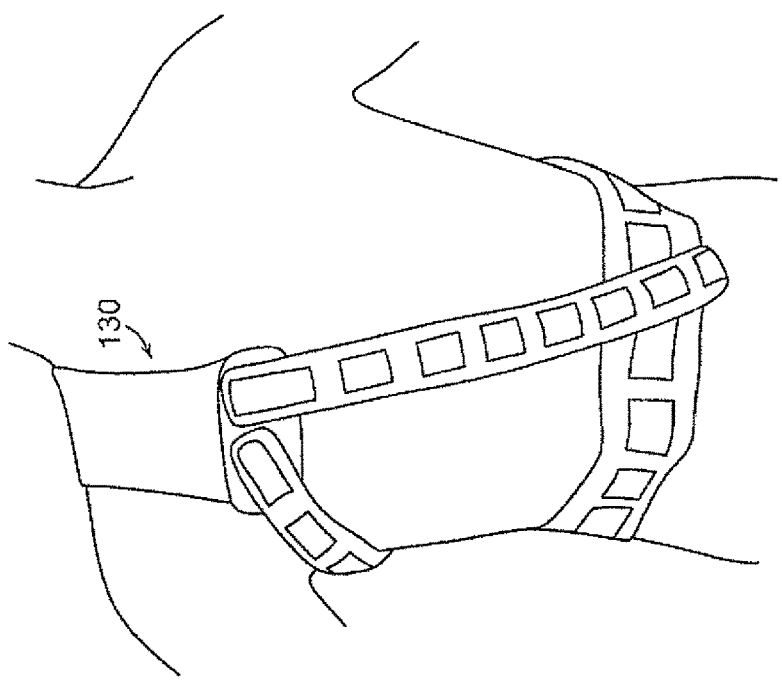

Allowing the LDD to work on small and large surfaces areas is possible with the flexibility of the device. But to naturally hold the LDD to the patient, particularly for complex body shapes such as the chest requires a precision holding device during treatment if the LDD is not embedded into a skin adhesive bandage as previously described. FIGS. 12A-12B show a LDD chest harness 130 using non-flammable and biocompatible components that can hold the LDD for Breast Cancer cases.

Figure 13B:
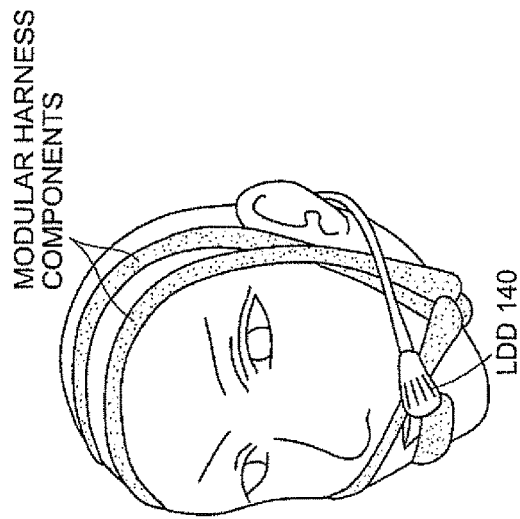
FIGS. 13A-13C are schematic diagrams illustrating harnesses for the ear, face, and nose having a LDD formed in accordance with the invention.
Figure 13C:
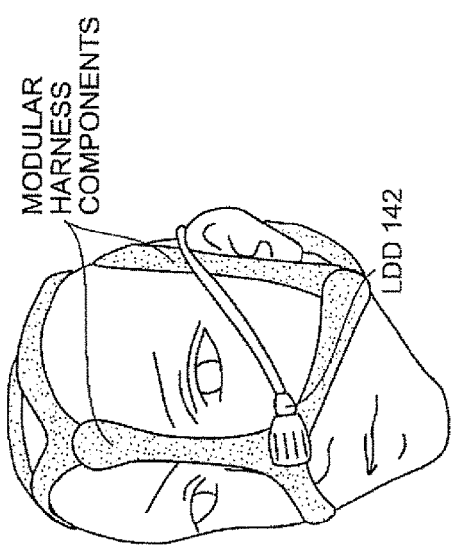
Figure 13A:
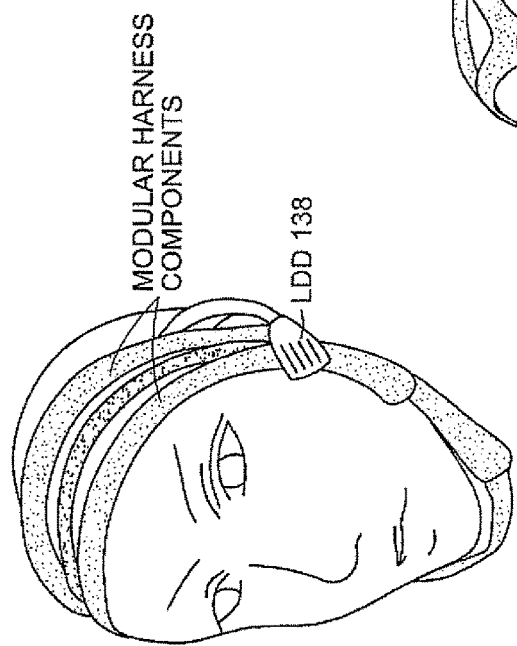

The harness for other large external body areas may be similar. For smaller body areas, FIG. 13A-13C show LDD harnesses 138, 140, 142 for the ear, face and nose. Moreover, it is possible to provide harnesses for hands and toes with LDD based gloves and socks.

The inventive LDD can be used as an implantable illuminator for Ovarian Cancer, hence the invention has both external (skin or the like) and internal (ovarian, prostate, esphogeal, or the like) applications.

Although the present invention has been shown and described with respect to several preferred embodiments thereof, various changes, omissions and additions to the form and detail thereof, may be made therein, without departing from the spirit and scope of the invention.

What is claimed is:

1. A system for photodynamic therapy comprising:
a light delivery device that delivers illumination necessary to perform continuous low irradiance photodynamic therapy, the light delivery device includes a 10 cm×10 cm wide pad, within the pad a plurality etched fibers are arranged in a one-dimensional array, to illuminate a selective region of a body for continuous low irradiance photodynamic therapy, said etched fibers in the pad are positioned in a bandage structure to form a light bandage, said light bandage comprises said etched fibers positioned between a first fluid absorbing layer and a second fluid absorbing layer, said bandage includes a light blocking layer after the second fluid absorbing layer, wherein said etched fibers comprise a plurality of optical fibers whose core and cladding are etched along one plane of fiber to control the release of light in a manner along the length of each etched fiber so as to produce a light pattern; and
an illumination device that is coupled to said etched fibers of said light delivery device using an optical coupler, said illumination device includes an illumination unit that houses a plurality of components to reduce heat from said illumination, wherein the light delivery device allows control of light exitance from the light bandage to within +/−20% of average irradiance, where said illumination device comprises a lens structure to produce an illumination beam having a Gaussian light intensity profile, wherein an etched pattern formed collectively by the plurality of etched fibers achieves the effect of a reverse Gaussian profile causing more uniform light intensity across the light bandage pad by suppressing the light intensity in the center of the light bandage pad to closely match the light intensity along the edges of the light bandage pad wherein said etched fibers are positioned into a circular bundle where they are coupled to said light delivery device, said circular bundle matches the beam diameter of said illumination beam, the illumination device being coupled to a battery holder and AC charger.

2. The system of claim 1, wherein the light delivery device has a bend radius of less than 12 cm.

3. The system of claim 1, wherein the one or more etched fibers are etched using a laser cutter arrangement.

4. The system of claim 1, wherein the one or more etched fibers comprise shapes so as to provide even illumination.

5. The system of claim 1, wherein the light delivery device is positioned on an anatomical region using one or more harnesses for support.

6. A method for performing photodynamic therapy comprising: delivering illumination necessary to perform continuous low irradiance photodynamic therapy to an anatomical region using a light delivery device, wherein the light delivery device includes a 10 cm×10 cm wide pad, within the pad a plurality etched fibers are arranged in a one-dimensional array, said etched fibers in the pad are positioned in a bandage structure to form a light bandage, said light bandage comprises said etched fibers positioned between a first fluid absorbing layer and a second fluid absorbing layer, said bandage includes a light blocking layer after the second fluid absorbing layer, wherein said etched fibers comprise a plurality of optical fibers whose core or and cladding are etched along one plane of fiber to control the release of light in a manner along the length of each etched fiber so as to produce a light pattern; and
coupling said etched fibers of said light delivery device to an illumination device using an optical coupler, said illumination device includes an illumination unit that houses a plurality of components to reduce heat from said illumination, wherein the light delivery device allows control of light exitance from the light bandage to within +/−20% of average irradiance, where said illumination device comprises a lens structure to produce an illumination beam having a Gaussian light intensity profile, wherein an etched pattern formed collectively by the plurality of etched fibers achieves the effect of a reverse Gaussian profile causing more uniform light intensity across the light bandage pad by suppressing the light intensity in the center of the light bandage pad to closely match the light intensity along the edges of the light bandage pad, wherein said etched fibers are positioned into a circular bundle where they are coupled to said light delivery device, said circular bundle matches the beam diameter of said illumination beam, the illumination device being coupled to a battery holder and AC charger.

7. The system of claim 6, wherein the light delivery device has a bend radius of less than 12 cm.

8. The method of claim 6, wherein the one or more etched fibers are etched using a laser cutter arrangement.

9. The method of claim 6, wherein the one or more etched fibers comprise a plurality of shapes so as to provide even illumination.

10. The method of claim 6, wherein the light delivery device is positioned on the anatomical region using one or more harnesses for support.

* * * * *